(12) United States Patent
Salehi-Had

(10) Patent No.: US 12,023,278 B1
(45) Date of Patent: Jul. 2, 2024

(54) DEVICES FOR PERFORMING INTRAOCULAR SURGERY AND METHODS FOR USING THEM

(71) Applicant: Hani Salehi-Had, Huntington Beach, CA (US)

(72) Inventor: Hani Salehi-Had, Huntington Beach, CA (US)

( * ) Notice: Subject to any disclaimer, the term of this patent is extended or adjusted under 35 U.S.C. 154(b) by 463 days.

(21) Appl. No.: 17/373,663

(22) Filed: Jul. 12, 2021

Related U.S. Application Data

(60) Provisional application No. 63/179,213, filed on Apr. 24, 2021.

(51) Int. Cl.
*A61F 9/007* (2006.01)
*A61B 18/08* (2006.01)

(52) U.S. Cl.
CPC ........ *A61F 9/00736* (2013.01); *A61B 18/082* (2013.01); *A61B 2218/007* (2013.01)

(58) Field of Classification Search
CPC ............... A61F 9/00736; A61B 18/082; A61B 2218/007
See application file for complete search history.

(56) References Cited

U.S. PATENT DOCUMENTS

| | | | | |
|---|---|---|---|---|
| 4,014,333 | A * | 3/1977 | McIntyre | A61F 9/00736 604/167.01 |
| 2015/0148615 | A1* | 5/2015 | Brennan | A61B 3/16 128/853 |
| 2019/0388135 | A1* | 12/2019 | Gogolin | A61B 18/1477 |
| 2021/0228412 | A1* | 7/2021 | de Juan | A61B 18/1485 |

* cited by examiner

*Primary Examiner* — Scott M. Getzow
(74) *Attorney, Agent, or Firm* — William A. English; Vista IP Law Group LLP

(57) ABSTRACT

Devices, systems, and methods for performing intraocular surgery. In one example, the device includes a handpiece including proximal and distal ends; a diathermy needle extending from the distal end and terminating in a diathermy tip; and a tubular shaft extending from the distal end adjacent the diathermy needle and terminating in an aspiration tip, the tubular shaft including an aspiration lumen extending proximally from an aspiration opening in the aspiration tip. An actuator on the handpiece is coupled to the shaft for directing the shaft between a distal position where the aspiration tip is adjacent the diathermy tip and a proximal position where the aspiration tip is offset proximally from the diathermy tip. A generator may be connected to the handpiece for delivering energy to the tip for performing diathermy and a vacuum source may be connected to the handpiece for delivering suction to the aspiration opening.

22 Claims, 2 Drawing Sheets

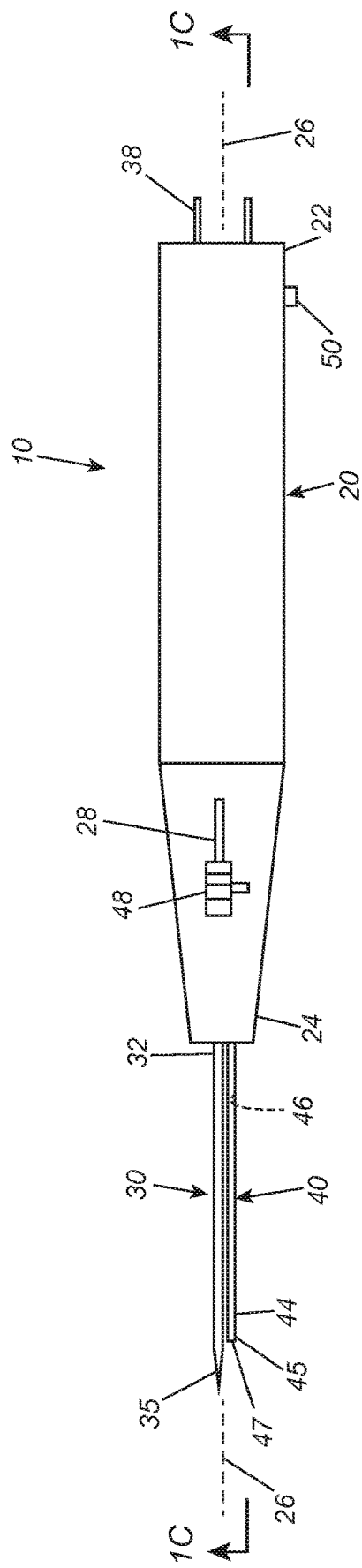
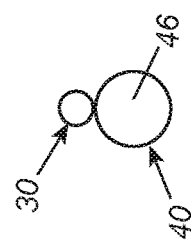
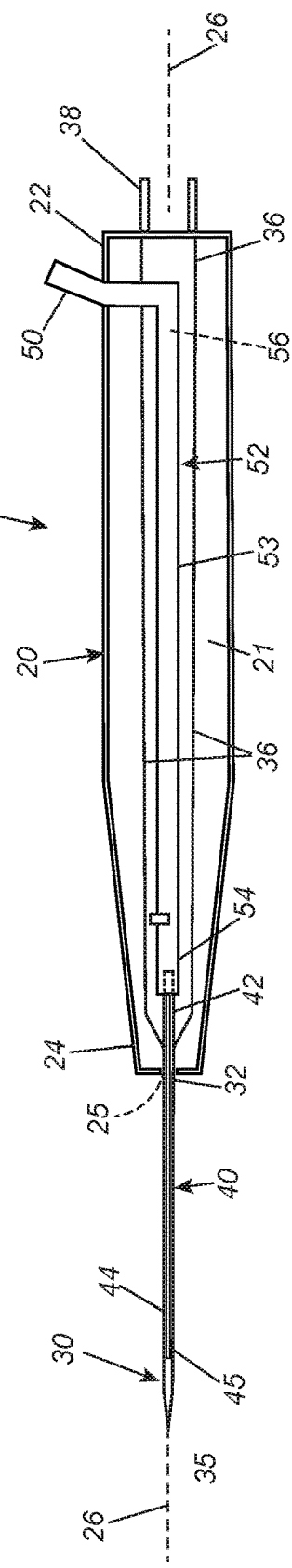
FIG. 1A
FIG. 1B
FIG. 1C

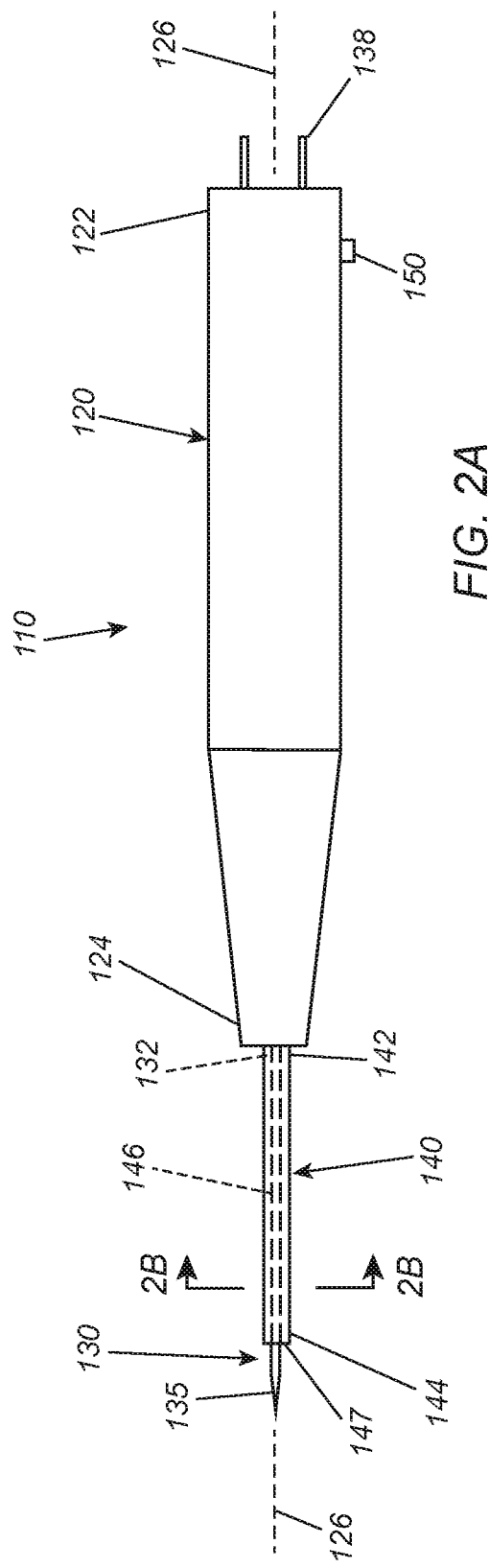
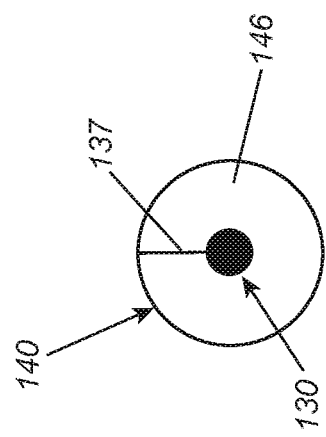
FIG. 2A
FIG. 2B

DEVICES FOR PERFORMING INTRAOCULAR SURGERY AND METHODS FOR USING THEM

RELATED APPLICATION DATA

The present application claims benefit of U.S. provisional application Ser. No. 63/179,213, filed Apr. 24, 2021, the entire disclosure of which is expressly incorporated by reference herein.

FIELD OF THE INVENTION

The present application generally relates to medical devices and, more particularly, to surgical instruments for performing intraocular surgery, e.g., a diathermy needle device that includes multiple tips to enable performing diathermy and aspiration using a single device, and to systems and methods for using such devices.

BACKGROUND

Diathermy is electrically induced heat, e.g., generated using radiofrequency or other electromagnetic energy, commonly used in surgical procedures. For example, during intraocular procedures, a diathermy needle may be introduced into the vitreous cavity of an eye through a trocar or cannula during a procedure, e.g., to cauterize bleeding vessels. During such procedures, multiple trocars are generally placed in the eye to allow different instruments to be introduced and manipulated simultaneously. Manipulating multiple instruments via different trocars, however, can be complicated. Alternatively, one instrument may need to be removed and another introduced to perform diathermy, during which time bleeding vessels will continue to bleed and compromise visualization of the surgical field.

In the view of the foregoing, devices that may facilitate intraocular surgery, e.g., potentially reducing the number of trocars and/or instruments needed or eliminate the need for an instrument exchange during intraocular surgery, would be useful.

SUMMARY

The present application is directed to medical devices and, more particularly, to surgical instruments for performing intraocular surgery, e.g., a diathermy needle device that includes multiple tips to enable performing diathermy and aspiration using a single device, and to systems and methods for using such devices.

In accordance with an exemplary aspect, a device is provided for performing intraocular surgery that includes a handpiece comprising a proximal end and a distal end, and defining a longitudinal axis therebetween; a diathermy needle extending axially from the distal end and terminating in a diathermy tip; a tubular shaft extending axially from the distal end adjacent the diathermy needle and terminating in an aspiration tip, the tubular shaft comprising an aspiration lumen extending proximally from an aspiration opening in the aspiration tip; and an actuator on the handpiece coupled to the tubular shaft for directing the tubular shaft between a distal position where the aspiration tip is adjacent the diathermy tip and a proximal position where the aspiration tip is offset proximally from the diathermy tip.

In accordance with another aspect, a method is provided for performing intraocular surgery that includes providing a diathermy device including a diathermy needle extending axially from handpiece and terminating in a diathermy tip, and a tubular shaft extending axially from the handpiece adjacent the diathermy needle and terminating in an aspiration tip; introducing the diathermy tip and aspiration tip into a vitreous cavity of an eye; manipulating the device to position the aspiration tip proximal to the diathermy tip; contacting tissue within the eye with the diathermy tip to deliver heat; manipulating the device to position the aspiration tip adjacent the diathermy tip; and aspirating material from the vitreous cavity into the aspiration tip and aspiration lumen.

In accordance with still another aspect, a device is provided for performing intraocular surgery that includes a handpiece comprising a proximal end and a distal end, and defining a longitudinal axis therebetween; a tubular shaft extending axially from the distal end and terminating in an aspiration tip, the tubular shaft comprising an aspiration lumen extending proximally from an aspiration opening in the aspiration tip; a diathermy needle extending axially from the distal end within the aspiration lumen and terminating in a diathermy tip that extends distally beyond the aspiration tip; a connector on the handpiece and one or more leads electrically coupling the connector to the diathermy needle, the connector configured for connecting to a diathermy generator to deliver diathermy to tissue contacted by the diathermy tip; and a port on the handpiece and a suction path communicating between the port and the aspiration lumen, the port configured for connecting to a source of vacuum for aspirating material into the aspiration opening and through aspiration lumen and port.

In accordance with yet another aspect, a system is provided for performing intraocular surgery that includes a diathermy device comprising a handpiece comprising a proximal end and a distal end, and defining a longitudinal axis therebetween; a tubular shaft extending axially from the distal end and terminating in an aspiration tip, the tubular shaft comprising an aspiration lumen extending proximally from an aspiration opening in the aspiration tip; and a diathermy needle extending axially from the distal end within the aspiration lumen and terminating in a diathermy tip that extends distally beyond the aspiration tip, the diathermy tip electrically coupled to a connector on the handpiece; and a diathermy generator connectable to the connector on the handpiece, the generator configured to generate electromagnetic signals that are transmitted to the diathermy tip to deliver diathermy to tissue contacted by the diathermy tip.

In accordance with still another aspect, a method is provided for performing intraocular surgery using a diathermy device including a diathermy needle extending axially from a handpiece and terminating in a diathermy tip, and a tubular shaft extending axially from the handpiece adjacent the diathermy needle and terminating in an aspiration tip, the method including introducing the diathermy tip and aspiration tip into a vitreous cavity of an eye; manipulating the device to position the aspiration tip proximal to the diathermy tip; contacting tissue within the eye with the diathermy tip to deliver heat; manipulating the device to position the aspiration tip adjacent the diathermy tip; and aspirating material from the vitreous cavity into the aspiration tip and aspiration lumen.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures:

FIG. 1A is a side view of an example of a device for performing intraocular surgery including a handpiece carrying a diathermy needle and a retractable aspiration shaft beside one another.

FIG. 1B is an end view of the device of FIG. 1A.

FIG. 1C is a longitudinal cross-section of the device of FIG. 1A taken along 1C-1C.

FIG. 2A is a side view of another example of a device for performing intraocular surgery including a handpiece carrying a diathermy needle and a retractable aspiration shaft concentrically around the diathermy needle.

FIG. 2B is a cross-sectional view of the device of FIG. 2A.

DETAILED DESCRIPTION

Before the exemplary devices, systems, and methods are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Turning to the drawings, FIGS. 1A-1C show an example of a diathermy device 10 that may be used during an intraocular procedure. Generally, the device 10 includes a handpiece 20 including a proximal end 22 and a distal end 24, thereby defining a longitudinal axis 26 therebetween, and a pair of shafts extending from the handpiece 20 including elements for performing one or more functions during the procedure. As shown, the device 10 includes a diathermy needle shaft 30 extending axially from the distal end 24 and terminating in a diathermy tip 35, and a tubular aspiration shaft 40 extending axially from the distal end 24 adjacent the needle shaft 30 and terminating in an aspiration tip 45. The aspiration shaft 40 includes an aspiration lumen 46 extending proximally from an aspiration opening or port 47 in the aspiration tip 45 and communicating with a suction path 52 within the handpiece 20. The shafts 30, 40 may be placed immediately adjacent one another, e.g., such that they may be introduced into a subject's eye through a single trocar or cannula (not shown), as described elsewhere herein.

At least one of the shafts 30, 40 is movable relative to the other, e.g., such the function and/or action of the device 10 may be selected and/or alternated, as desired during a procedure. For example, as shown in FIG. 1B, an actuator 48 on the handpiece 20 may be coupled to the aspiration shaft 40 for directing the shaft 40 between a distal position, e.g., where the aspiration tip 45 is adjacent the diathermy tip 35, and a proximal position, e.g., where the aspiration tip 45 is offset proximally from the diathermy tip 35 (not shown). In one example, the actuator includes a button 48 slidably mounted on the handpiece 20, e.g., within a track 28, and movable axially between first and second positions for moving the aspiration shaft 40 between the distal and proximal positions. Alternatively, it will be appreciated that other actuators may be provided, such as a rotating dial and the like (not shown) that may be mechanically coupled to the aspiration shaft 40 to move the shaft 40 axially. In a further alternative, the aspiration shaft may be fixed relative to the handpiece 20 and the diathermy needle 30 may be movable axially relative to the handpiece 20.

As shown in FIGS. 1A and 1B, in the distal position, the aspiration tip 45 may be positioned immediately adjacent the diathermy tip 35, e.g., such that material immediately adjacent the diathermy tip 35 may be aspirated into the aspiration lumen 46, as described further elsewhere herein. Alternatively, the aspiration tip 45 may be offset distally or proximally relative to the diathermy tip 35 in the distal position. In the proximal position, the aspiration tip may be offset proximally from the diathermy tip 35, e.g., by between about one to five millimeters (1.0-5.0 mm). Optionally, the handpiece 20 may include a valve or other actuator (not shown) to open a path between the aspiration opening 47 and the source of vacuum, e.g., to control the pressure of the suction during use. Alternatively, the path may remain open and the source of vacuum may be activated or otherwise used to selectively apply a suction to the aspiration port 47 and lumen 46.

In the example shown in FIGS. 1A-1B, a proximal end 32 of the needle shaft 30 is fixedly attached to the distal end 24 of the handpiece 20, e.g., by one or more of bonding with adhesive, fusing, cooperating connectors, and the like. The needle shaft 30 may be formed from one or more substantially rigid or malleable tubular or solid elongate members of biocompatible material, e.g., metal such as stainless steel, aluminum, and the like, plastic, or composite materials. For example, as shown, the needle shaft 30 may be a rigid solid needle terminating in a pointed or sharpened tip 35. The entire needle shaft 30 may be electrically conductive, or may include one or more discrete electrodes (not shown), e.g., at the tip 35, while the remainder of the shaft 30 is electrically insulated. Alternatively, the needle shaft 30 may provide a first electrode and the aspiration shaft 40 may provide a second electrode (not shown). The needle 30 (or electrodes) may be electrically coupled to a generator or other power source (not shown) via one or more leads, e.g., a pair of wires 36, to deliver electrical energy to the tip 35 to perform diathermy, as described further elsewhere herein. In this configuration, the needle 30 may be used in a bipolar configuration to delivery diathermy, although, alternatively, the needle 30 may be configured in a unipolar configuration, e.g., with a single electrode and lead on the device 10 and another ground or common electrode coupled to the subject's body, e.g., an electrical pad that may be secured to the patient's skin (not shown), as is known in the art.

With particular reference to FIG. 1B, the distal end 24 of the handpiece may include a passage or opening 25 communicating with an interior cavity 21 of the handpiece 20 immediately adjacent the proximal end 32 of the needle shaft 30, which is sized to slidably receive a proximal end 42 of the aspiration shaft 40. The aspiration shaft 40 may be formed from a rigid or malleable tubular body of biocompatible material, e.g., metal, plastic, or composite material that is slidably received through the passage 25. The distal tip 45 of the aspiration shaft 40 may have a substantially blunt shape with an opening 47, e.g., aligned with the longitudinal axis 26.

The shafts 30, 40 may be positioned immediately adjacent one another such that the aspiration shaft 40 slides along an outer surface of the needle shaft 30, which may minimize an overall cross-section of the shafts 30, 40. This may allow the device 10 to be introduced through a smaller trocar into a subject's eye. For example, the shafts 30, 40 may be introduced through a conventional trocar or cannula, e.g., a 25 or 23 gauge trocar (not shown), which may have an inner diameter between about 0.260-0.337 millimeter. Alternatively, the aspiration shaft 40 may be spaced apart such that it does not contact the needle shaft 30. For example, the aspiration shaft 40 may have an outer diameter between about 0.2-0.3 millimeter, and the needle shaft 30 may have a smaller outer diameter than the aspiration shaft 40.

The handpiece 20 may have a size and/or shape to facilitate holding and/or manipulating the device 10 during use, e.g., including a cylindrical or otherwise shaped grip portion (not shown). Optionally, one or more ridges, recesses, or other grip features may be provided on the outer surface, e.g., adjacent the proximal end 22. The handpiece 20 may include one or more connectors for coupling the device 10 to one or more external devices, e.g., a diathermy generator and/or source of vacuum or suction (not shown), e.g., to provide a system that may be used during a surgical procedure. For example, as shown, the device 10 may include an electrical connector 38 on the handpiece 20, e.g., on the proximal end 22, that is electrically coupled to the diathermy tip 35 via the leads 36 and configured for connecting to a diathermy generator or other power source (not shown) to deliver diathermy to tissue contacted by the diathermy tip 35. For example, the wires 36 may extend distally from the connector 38 axially within the cavity 21 of the handpiece 20 to the needle shaft 30 and may be electrically coupled to the diathermy tip 35, e.g., to respective electrodes (not shown) on or adjacent the tip 35.

Optionally, the handpiece 20 may include a switch or other mechanism (not shown) that may be actuated by the user to selectively deliver energy to the diathermy tip 35. For example, the handpiece 20 may include a knob or other actuator (not shown) that may be squeezed or otherwise manipulated to deliver diathermy and/or to control the intensity of the energy delivered. In addition or alternatively, the generator may include a switch or other mechanism, e.g., a foot pedal (not shown), that may be actuated by the user to selectively deliver energy to the diathermy tip 35, e.g., that may be pressed with the operator's foot to control the intensity of the heat delivered. Alternatively, the foot pedal may be used to control the suction, e.g., pressed by the operator's foot to control the pressure of the suction. Thus, any combination of actuators on the handpiece 20 or on a foot pedal or other separate actuator may be provided to control diathermy and suction, as desired.

In addition or alternative, the handpiece 20 may include a port 50 on the handpiece 20 communicating with the aspiration lumen 46 via suction path 52 and configured for connecting to a source of vacuum (not shown) for aspirating material into the aspiration opening 47 and through aspiration lumen 46 and port 50 to the source. For example, the port 50 may include a male or female Luer fitting (not shown), which may be connected to a line of tubing and the like that may be connected, in turn, to a source of vacuum, e.g., a pump, vacuum line, syringe, and the like (also not shown).

In one example, the handpiece 20 may include one or more tubular members defining the suction path 52 communicating between the port 50 and the aspiration lumen 46. For example, as best seen in FIG. 1B, a length of tubing 53 may be mounted within the cavity 21 of the handpiece 20 that extends axially at least partially between the proximal end 22 and the distal end 24 of the handpiece 20, which may at least partially define the suction path 52. In one example, the aspiration shaft 40 may include a proximal end 42 sliding telescopically with a distal end 54 of the tubing 53 such that the aspiration lumen 46 communicates through an interior lumen 56 of the tubing 53 with the port 50.

For example, as shown in FIG. 1C, the proximal end 42 of the shaft 44 may be slidably received within the distal end 54 of the tubing 53, e.g., to accommodate axial movement of the aspiration shaft 40 between the proximal and distal positions while maintaining a path for aspiration. In one example, the tubing 53 may be formed from elastomeric or other flexible material to accommodate movement of the proximal end 42 of the aspiration shaft 40 therein while provide a substantially fluid-tight seal. In addition or alternatively, one or both of the proximal end 42 of the shaft 40 and the distal end 54 of the tubing 53 may include one or more seals, e.g., one or more O-rings (not shown), to provide a fluid-tight seal. In another alternative, a length of flexible tubing may be permanently connected to the proximal end 42 of the aspiration shaft 40 and connected to the port 50, e.g., such that the tubing may curve or straighten as needed to accommodate axial movement of the aspiration shaft 40 while providing the suction path 52.

During use, the device 10 may be used during a surgical procedure to delivery diathermy and/or aspirate material using a single device 10. For example, during an intraocular surgical procedure, one or more trocars or cannulas (not shown) may be introduced into an eye to provide access to the vitreous cavity (also not shown). The device 10 may be prepared in a conventional manner, e.g., by connecting a RF generator or other power source (not shown) to the connector 38 and by connecting a source of vacuum/suction (also not shown) to the port 50. The needle shaft 30 and aspiration shaft 40 may then be introduced through one of the trocars into the vitreous cavity. The device 10 may be used alone or in cooperation with one or more other instruments, e.g., introduced into one or more separate trocars or cannulas (not shown).

When desired, the device 10 may be used to perform diathermy, e.g., to cauterize blood vessels within the eye or otherwise deliver heat to target tissues within the eye. For example, initially, the device 10 may introduced with the aspiration shaft 40 in the proximal position such that the needle shaft 30 may be manipulated by holding the handpiece 20 and used to deliver diathermy via the diathermy tip 35, similar to conventional diathermy instruments (e.g., controlled by an actuator on the handpiece 20 or a foot pedal or other separate actuator, not shown). When desired, the actuator 48 may be manipulated to advance the aspiration shaft 40 to position the aspiration port 47 adjacent the diathermy tip 35. The source of vacuum may then be activated (e.g., by a foot pedal or a valve in the handpiece 20 manipulated) to apply a suction to the aspiration port 47 and lumen 46 to aspirate material within the cavity. After aspiration, the shaft 40 may be directed to the proximal position, e.g., to allow further diathermy using the needle 30.

Upon completion of the procedure, the device 10 and any other instruments may be removed using conventional methods.

Turning to FIGS. 2A and 2B, another example of a diathermy device 110 is shown that includes a handpiece 120 including a diathermy needle shaft 130 and a tubular aspiration shaft 140 positioned concentrically around the needle shaft 130. In this example, the needle shaft 130 and aspiration shaft 140 may be fixed relative to the handpiece 120, e.g., by attaching their proximal ends 132, 142 to the distal end 124 of the handpiece 120.

In this example, the needle shaft 130 may have a length longer than the aspiration shaft 140 such that the diathermy tip 135 extends distally beyond an aspiration opening 147 in the aspiration shaft 140. As best sent in FIG. 2B, the aspiration shaft 140 may have an inner diameter or other cross-section larger than an outer diameter or cross-section than that needle shaft 130 such that material may be aspirated through the aspiration lumen 146 around the needle 130.

The needle shaft 130 may include one or more electrodes, e.g., by constructing the needle shaft 130 from electrically conductive material or providing one or more discrete electrodes (not shown) on or adjacent the diathermy tip 135, e.g., as described previously, to provide a bipolar or unipolar configuration for delivering diathermy. Optionally, the aspiration shaft 140 may be electrically coupled to the needle shaft 130, e.g., adjacent the diathermy tip 135 to deliver electrical energy from a power source to the diathermy tip 135. For example, as shown in FIG. 2B, a wire, lead, or other electrically conductive connection 137 may be provided that extends between the aspiration shaft 140 to the needle shaft 130, e.g., adjacent the distal tip 135, to deliver electrical energy to the diathermy tip 135. In this example, one or more wires or electrical leads (not shown) may be embedded within or otherwise extend proximally from the connection 137 into the handpiece 120, which may, in turn, be coupled to one more leads (also not shown) within the handpiece 120 and coupled to the connector 138, similar to the device 10.

The device 110 may be used similar to the device 10, e.g., by simultaneously introducing the diathermy and aspiration shafts 130, 140 into a vitreous cavity of an eye and used to perform diathermy and suction material, as desired, during a procedure. However, the shafts 130, 140 may be fixed such that no manipulation of the aspiration shaft 140 is needed. The relative size of the shafts 130, 140 may provide an aspiration lumen 146 between them that is sufficiently large to aspirate material adjacent the diathermy tip 135 into the opening 147 and aspiration lumen 146.

Although the devices herein have been described with particular reference to intraocular procedures, it will be appreciated that the devices may be used in other procedures, e.g., where the shafts of the device are introduced through a trocar, cannula, or other port into a region of a subject's body to perform diathermy and aspiration.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A device for performing intraocular surgery, comprising:
   a handpiece comprising a proximal end and a distal end, and defining a longitudinal axis therebetween;
   a diathermy needle extending axially from the distal end and terminating in a diathermy tip;
   a tubular shaft extending axially from the distal end adjacent the diathermy needle and terminating in an aspiration tip, the tubular shaft comprising an aspiration lumen extending proximally from an aspiration opening in the aspiration tip; and
   an actuator on the handpiece coupled to the tubular shaft for directing the tubular shaft between a distal position where the aspiration tip is adjacent the diathermy tip and a proximal position where the aspiration tip is offset proximally from the diathermy tip.

2. The device of claim 1, further comprising a connector on the handpiece electrically coupled to the diathermy tip and configured for connecting to a diathermy generator to deliver diathermy to tissue contacted by the diathermy tip.

3. The device of claim 2, further comprising one or more leads extending from the connector to the diathermy needle and electrically coupled to the diathermy tip.

4. The device of claim 1, further comprising a port on the handpiece and a suction path communicating between the port and the aspiration lumen, the port configured for connecting to a source of vacuum for aspirating material into the aspiration opening and through aspiration lumen and port.

5. The device of claim 4, further comprising a length of tubing extending axially at least partially between the handpiece proximal and distal ends and at least partially defining the suction path, the tubular shaft comprising a proximal end sliding telescopically with a distal end of the tubing such that the aspiration lumen communicates with an interior of the tubing.

6. The device of claim 5, wherein the proximal end of the tubular shaft is slidably received within the distal end of the tubing.

7. The device of claim 5, wherein one or both of the proximal end of the tubular shaft and the distal end of the tubing comprise one or more seals to provide a fluid-tight seal.

8. The device of claim 1, wherein the actuator comprises a button slidably mounted on the handpiece and movable axially between first and second positions for moving the tubular shaft between the distal and proximal positions.

9. The device of claim 1, wherein the aspiration shaft is configured to slide along an outer surface of the diathermy needle.

10. A system for performing intraocular surgery, comprising:
    a diathermy device comprising:
    a) a handpiece comprising a proximal end and a distal end, and defining a longitudinal axis therebetween;
    b) a diathermy needle extending axially from the distal end and terminating in a diathermy tip, the diathermy tip electrically coupled to a connector on the handpiece;
    c) a tubular shaft extending axially from the distal end adjacent the diathermy needle and terminating in an aspiration tip, the tubular shaft comprising an aspiration lumen extending proximally from an aspiration opening in the aspiration tip; and
    d) an actuator on the handpiece coupled to the tubular shaft for directing the tubular shaft between a distal position where the aspiration tip is adjacent the diathermy tip and a proximal position where the aspiration tip is offset proximally from the diathermy tip; and a diathermy generator connectable to the connector on the handpiece, the generator configured to generate electromagnetic signals that are transmitted to the diathermy tip to deliver diathermy to tissue contacted by the diathermy tip.

11. The system of claim 10, wherein the handpiece comprises a port and a suction path communicating between the port and the aspiration lumen, the system further comprising a vacuum source connectable to the port for aspirating material into the aspiration opening and aspiration lumen.

12. The system of claim 11, wherein the diathermy device further comprises a length of tubing extending axially at least partially between the handpiece proximal and distal ends and at least partially defining the suction path, the tubular shaft comprising a proximal end sliding telescopically with a distal end of the tubing such that the aspiration lumen communicates with an interior of the tubing.

13. The system of claim 12, wherein the proximal end of the tubular shaft is slidably received within the distal end of the tubing.

14. The system of claim 12, wherein one or both of the proximal end of the tubular shaft and the distal end of the tubing comprise one or more seals to provide a fluid-tight seal.

15. The system of claim 10, wherein the diathermy device further comprises one or more leads extending from the connector to the diathermy needle and electrically coupled to the diathermy tip.

16. The system of claim 10, wherein the diathermy needle is positioned adjacent the tubular shaft outside the aspiration lumen such that the aspiration shaft is configured to slide along an outer surface of the diathermy needle.

17. A method for performing intraocular surgery, comprising:
providing a diathermy device including a diathermy needle extending axially from a handpiece and terminating in a diathermy tip, and a tubular shaft extending axially from the handpiece adjacent the diathermy needle and terminating in an aspiration tip;
introducing the diathermy tip and aspiration tip into a vitreous cavity of an eye;
manipulating the device to position the aspiration tip proximal to the diathermy tip;
contacting tissue within the eye with the diathermy tip to deliver heat with the aspiration tip positioned proximal to the diathermy tip;
manipulating the device to move the tubular shaft relative to the needle to position the aspiration tip adjacent the diathermy tip; and
aspirating material from the vitreous cavity into the aspiration tip and aspiration lumen with the aspiration tip adjacent the diathermy tip.

18. The method of claim 17, wherein the aspiration tip is positioned proximal to the diathermy tip before introducing the diathermy tip and aspiration tip into the vitreous cavity.

19. The method of claim 17, wherein manipulating the device to position the aspiration tip adjacent the diathermy tip comprises manipulating an actuator on a handpiece of the device to advance the aspiration tip until the aspiration tip is adjacent or distally beyond the diathermy tip.

20. The method of claim 17, wherein tissue is contacted with the diathermy tip to deliver heat with the aspiration tip spaced proximally from the diathermy tip, and wherein manipulating the device comprises advancing the tubular shaft relative to the needle to position the aspiration tip adjacent the diathermy tip before aspirating material.

21. A device for performing intraocular surgery, comprising:
a handpiece comprising a proximal end and a distal end, and defining a longitudinal axis therebetween;
a tubular shaft extending axially from the distal end and terminating in an aspiration tip, the tubular shaft comprising an aspiration lumen extending proximally from an aspiration opening in the aspiration tip;
a diathermy needle extending axially from the distal end adjacent the tubular shaft outside the aspiration lumen and terminating in a diathermy tip positioned adjacent the aspiration tip;
a connector on the handpiece and one or more leads electrically coupling the connector to the diathermy needle, the connector configured for connecting to a diathermy generator to deliver diathermy to tissue contacted by the diathermy tip; and
a port on the handpiece and a suction path communicating between the port and the aspiration lumen, the port configured for connecting to a source of vacuum for aspirating material into the aspiration opening and through aspiration lumen and port.

22. The device of claim 21, further comprising an actuator on the handpiece coupled to the tubular shaft for directing the tubular shaft between a distal position where the aspiration tip is adjacent the diathermy tip to aspirate and a proximal position where the aspiration tip is offset proximally from the diathermy tip to deliver diathermy.

* * * * *